United States Patent [19] [11] 4,363,920
Viscardi [45] Dec. 14, 1982

[54] PROCESS FOR THE PREPARATION OF N-[2-(-THENOYL)THIOPROPIONYL]-GLYCINE

[75] Inventor: Renzo Viscardi, Tribiano, Italy

[73] Assignee: B.T.B. Industria Chimica S.p.A., Tribiano, Italy

[21] Appl. No.: 266,965

[22] Filed: May 26, 1981

[30] Foreign Application Priority Data

Jun. 3, 1980 [IT] Italy ............................... 22516 A/80

[51] Int. Cl.³ ........................................... C07D 333/24
[52] U.S. Cl. ........................................ 549/72; 549/71
[58] Field of Search .................................. 549/71, 72

[56] References Cited

PUBLICATIONS

Wagner & Zook "Synthetic Organic Chem." (1965), pp. 566–569.

Primary Examiner—Alan Siegel
Attorney, Agent, or Firm—Bucknam and Archer

[57] ABSTRACT

N-[2-(2-thenoyl)thiopropionyl]-glycine is prepared, according to a process which is especially advantageous for the purity and the stability of the product, by means of N-acylation of glycine with an activated derivative of 2-(2-thenoyl)thiopropionic acid.

4 Claims, No Drawings

PROCESS FOR THE PREPARATION OF N-[2-(-THENOYL)THIOPROPIONYL]-GLYCINE

DESCRIPTION OF THE INVENTION

The invention relates to a new and improved process for the preparation of N-[2-(2-thenoyl)thiopropionyl]-glycine, of formula (I):

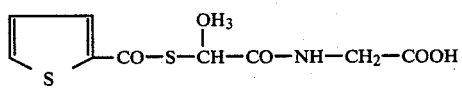

The compound (I), endowed with remarkable liver protective and mucolytic activity, is prepared according to the Italian Patent Application 22175 A/78, by reacting the thiophene-2-carboxylic acid chloride with N-(2-mercaptopropionyl)-glycine.

The Italian Patent Application 24534 A/79 claims another method for the preparation of (I) by reacting thiophene-2-thiolcarboxylic acid (under the form of salt with an alkali metal) and a N-(2-halopropionyl)-glycine. Both processes present some drawbacks, such as the high cost and the unpleasant smell of N-(2-mercaptopropionyl)-glycine, respectively of thiophene-2-thiolcarboxylic acid, and the difficulty to eliminate from the reaction product impurities which not only present unpleasant smell, but catalyze the decomposition of compound (I).

It has now surprisingly been found that N-[2-(2-thenoyl)thiopropionyl]-glycine (I) can be obtained with high yields, starting from odourless compounds, and at a state of high purity, by means of reaction of an activated derivative of 2-(2-thenoyl)thiopropionic acid (II) with glycine (III) according to the scheme:

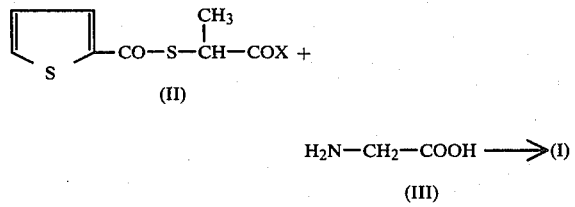

in which X represents any activating group which is able to form the amidic bound of compound (I).

In particular, X can represent halo, for example chlorine, or an alkoxy group or a residue such as to form an anhydride (homogeneous or mixed) with the thiophenecarbonilic residue, or the group

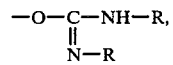

where R represents on its turn an alkyl or cycloalkyl residue, for example cyclohexenyl.

The 2-(2-thenoylthio)propionic acid (II, where X=OH) is, in its turn, easily obtained by means of acylation of thiolactic (or 2-mercaptopropionic) acid with 2-chlorocarbonyl-thiophene.

The acylation of the glycine with the compounds (I) is carried out at temperatures ranging from about 0° to about 30° C., preferably from about 5 to about 20° C., in different solvents according to the meaning of X. When X is such to make the compound (II) too sensible to the water, as in the case of a mixed anhydride or of the reaction product with dicyclohexylcarbodiimide, the reaction is carried out in aprotic solvents, such as haloalkanes, dimethylformamide, dimethylsulfoxide. In the case (particularly advantageous in this process) that X represents a chlorine atom, the reaction with glycine can be carried out also in aqueous medium, in the presence of acidity acceptors, such as hydroxides, carbonates or hydrogen carbonates of alkali or earth-alkali metals, or tertiary organic bases, such as triethylamine or pyridine.

The process according to the invention is illustrated but not limited by the following examples.

EXAMPLE 1

(a) 2-(2-thenoyl)thiopropionic acid

In a solution of 218 g (2 moles) of 2-mercaptopropionic acid and 790 g (5.7 moles) of $K_2CO_3$ in 2 liters of water, 293 g (2 moles) of thiophene-2-carboxylic acid chloride are added, under stirring and keeping the temperature under 20°–25° C. When the addition is completed stirring is continued for 4 hours, then it is put in a mixture of 850 ml of conc. HCl and 500 ml of $H_2O$.

The obtained mixture is shaken with 2 liters and then 1 liter of $CH_2Cl_2$. The collected organic extracts are dried on $MgSO_4$ and filtered. The solvent is evaporated. The oily residue crystallizes by scratching; yield 416 g (96%) of product which melts at 40°–42° C., whose analytic and spectroscopic characteristics agree with the ones foreseen for 2-(2-thenoyl)thiopropionic acid.

(b) To a solution of 21.6 g (0.1 mole) of 2-(2-thenoyl)thiopropionic acid and 7.5 g (0.1 mole) of glycine in 100 ml of dimethylsulfoxide, 20.6 g of N,N'-dicyclohexylcarbodiimide are added, under stirring, between 15° to 20° C. Stirring is continued for half an hour more, most of the solvent is evaporated under vacuum, 200 ml of water are added and the solution is taken to pH 9 with NaOH. Dicyclohexylurea is eliminated by filtration, then it is acidified with HCl. 14.2 g (yield 52%) of N-[2-(2-thenoyl)thiopropionyl]-glycine are obtained. The product is unitary in TLC.

EXAMPLE 2

In 150 ml of $CHCl_3$ 21.6 g (0.1 moles) of 2-(2-thenoyl)thiopropionic acid are dissolved, 10.1 g (0.1 moles) of triethylamine are subsequently added, and then, dropwise and cooling under 20° C., 12.05 g (0.1 mole) of ethylchlorocarbonate. After half an hour stirring 7.5 g (0.1 moles) of glycine are added, keeping the temperature under 20° C. After two hours the triethylamine hydrochloride is eliminated by filtration, 100 ml of water containing 0.11 moles of NaOH are added, the organic phase is separated and it is definetly acidified with HCl. 17.5 g (64%) of the wanted product precipitate, m.p. 169°–171° C., unitary in TLC.

EXAMPLE 3

At 216 g (1 mole) of 2-(2-thenoyl)thiopropionic acid in 2 liters of $CH_2Cl_2$, 119 g (1 mole) of $SOCl_2$ are added, under stirring and keeping the temperature under 30° C.

Stirring is continued for 6 hours, then the solvent is evaporated (finally under vacuum) to eliminate all the formed hydrogen chloride. The oily residue is dissolved in 400 ml of $CH_2Cl_2$ and is dropped in a 75 g (1 mole) of glycine and 276 g (2 moles) of $K_2CO_3$ solution, under strong stirring and keeping the temperature under 20° C. When the addition is ended, stirring is continued for 8 more hours, then the organic layer is eliminated, aqueous phase is acidified with HCl and the precipitate is pump-filtered and it is deeply washed with water, then with isopropanol. By drying, 196.6 g (72%) of product at m.p. 170°–171° C., unitary in TLC, are obtained.

By evaporation of the isopropanol used in the washing 43.2 g (20%) of 2-(2-thenoyl)thiopropionic acid are recovered.

I claim:

1. Process for the preparation of N-glycine (I) of formula:

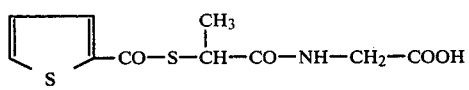

which consists of reacting glycine (III) with 2-(2-thenoyl)thiopropionic acid (II) of formula

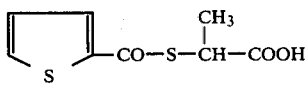

in the presence of N,N'-dicyclohexyl-carbodiimide at a temperature of 15°–20° C. in an aprotic solvent whereby said compound of formula (II) is converted in situ into the compound of formula (VI)

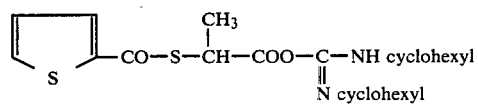

and the compound of formula (VI) reacts with glycine, then removing the solvent, adding water, making the reaction mixture basic, removing dicyclohexyl urea by filtration and isolating said product of formula (I) by acidification.

2. Process for the preparation of N-glycine (I) of formula:

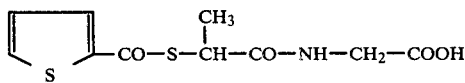

which consists of reacting 2-(2-thenoyl)thiopropionic acid (II) of formula

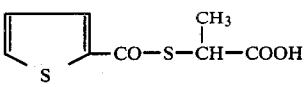

with a compound (IV) capable of converting said compound of formula (II) into a compound of formula (V)

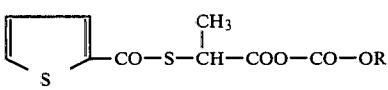

in which R is $C_1$–$C_4$ alkyl, in the presence of a tertiary amine, then reacting with glycine at a temperature lower than 20° C. and isolating the compound of formula (I) from the reaction mixture.

3. The process according to claim 2, wherein said compound (IV) capable of converting said compound of formula (II) into said compound of formula (V) is ethyl chlorocarbonate.

4. Process for the preparation of N-glycine (I) of formula:

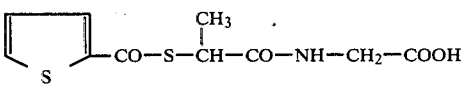

which consists of reacting 2-(2-thenoyl)thiopropionic acid (II) of formula

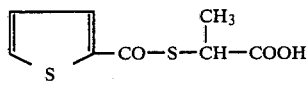

with thionyl chloride at a temperature lower than 30° C. and dissolving the acid chloride of said compound (II) thus formed in an anhydrous solvent to form a solution of the acid chloride of said compound II, and reacting said solution with glycine in the presence of an acid acceptor and isolating said compound of formula (I) from the reaction mixture.

* * * * *